United States Patent
Krapohl

(10) Patent No.: US 10,105,174 B2
(45) Date of Patent: Oct. 23, 2018

(54) METHOD FOR EMPLOYING SINGLE FAULT SAFE REDUNDANT SIGNALS

(71) Applicant: COVIDIEN LP, Mansfield, MA (US)

(72) Inventor: James E. Krapohl, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 2 days.

(21) Appl. No.: 15/194,643

(22) Filed: Jun. 28, 2016

(65) Prior Publication Data

US 2016/0302848 A1 Oct. 20, 2016

Related U.S. Application Data

(62) Division of application No. 13/442,460, filed on Apr. 9, 2012, now Pat. No. 9,375,250.

(51) Int. Cl.
*A61B 18/04* (2006.01)
*A61B 18/12* (2006.01)
(Continued)

(52) U.S. Cl.
CPC .. *A61B 18/1233* (2013.01); *A61B 17/320068* (2013.01); *A61B 18/1206* (2013.01); *A61B 18/18* (2013.01); *A61N 5/10* (2013.01); *A61B 2017/00026* (2013.01); *A61B 2017/00084* (2013.01); *A61B 2018/00642* (2013.01); *A61B 2018/00648* (2013.01); *A61B 2018/00666* (2013.01); *A61B 2018/00678* (2013.01); *A61B 2018/00708* (2013.01); *A61B 2018/00779* (2013.01); *A61B 2018/00791* (2013.01);
(Continued)

(58) Field of Classification Search
None
See application file for complete search history.

(56) References Cited

U.S. PATENT DOCUMENTS 5,438,302 A 8/1995 Goble
5,540,684 A 7/1996 Hassler, Jr.
(Continued)

FOREIGN PATENT DOCUMENTS

DE 179607 C 3/1905
DE 390937 C 3/1924
(Continued)

OTHER PUBLICATIONS

Anderson et al., "A Numerical Study of Rapid Heating for High Temperature Radio Frequency Hyperthermia" International Journal of Bio-Medical Computing, 35 (1994) pp. 297-307.
(Continued)

*Primary Examiner* — Eric D. Bertram
*Assistant Examiner* — Elizabeth K. So

(57) ABSTRACT

An electrosurgical system includes an electrosurgical instrument coupled to an electrosurgical generator. The electrosurgical system may include a first sensor and a second sensor, which are configured to detect redundant tissue properties and output a signal corresponding thereto. The electrosurgical system has a signal processing circuit for receiving and modifying the output signal from the second sensor. The electrosurgical generator may include a controller for receiving an output signal from the first sensor and a processed signal from the signal processing circuit. The controller compares the two signals received and shuts down the system based on the comparison of the first sensor and a processed signal.

20 Claims, 3 Drawing Sheets

(51) Int. Cl.
 *A61B 17/32* (2006.01)
 *A61B 18/18* (2006.01)
 *A61N 5/10* (2006.01)
 *G01R 31/40* (2014.01)
 *A61B 18/00* (2006.01)
 *A61B 17/00* (2006.01)

(52) U.S. Cl.
 CPC ............. *A61B 2018/00827* (2013.01); *A61B 2018/00869* (2013.01); *A61B 2018/00875* (2013.01); *A61B 2018/00892* (2013.01); *A61B 2018/00994* (2013.01); *G01R 31/40* (2013.01)

(56) References Cited

U.S. PATENT DOCUMENTS

| | | |
|---|---|---|
| 5,558,671 A | 9/1996 | Yates |
| 5,647,869 A | 7/1997 | Goble et al. |
| 5,702,386 A | 12/1997 | Stern et al. |
| 5,713,896 A | 2/1998 | Nardella |
| 5,722,975 A | 3/1998 | Edwards et al. |
| 5,733,281 A | 3/1998 | Nardella |
| 5,755,715 A | 5/1998 | Stern et al. |
| 5,830,212 A | 11/1998 | Cartmell et al. |
| 5,836,943 A | 11/1998 | Miller, III |
| 5,954,717 A | 9/1999 | Behl et al. |
| 6,016,445 A | 1/2000 | Baura |
| 6,058,325 A | 5/2000 | Baura |
| 6,093,186 A | 7/2000 | Goble |
| 6,123,701 A | 9/2000 | Nezhat |
| 6,142,992 A | 11/2000 | Cheng et al. |
| 6,193,713 B1 | 2/2001 | Geistert et al. |
| 6,235,020 B1 | 5/2001 | Cheng et al. |
| 6,238,387 B1 | 5/2001 | Miller, III |
| 6,245,065 B1 | 6/2001 | Panescu et al. |
| 6,253,103 B1 | 6/2001 | Baura |
| 6,254,600 B1 | 7/2001 | Willink et al. |
| 6,261,286 B1 | 7/2001 | Goble et al. |
| 6,293,942 B1 | 9/2001 | Goble et al. |
| 6,306,134 B1 | 10/2001 | Goble et al. |
| 6,358,246 B1 | 3/2002 | Behl et al. |
| 6,364,877 B1 | 4/2002 | Goble et al. |
| 6,416,509 B1 | 7/2002 | Goble et al. |
| 6,436,096 B1 | 8/2002 | Hareyama |
| 6,464,696 B1 | 10/2002 | Oyama et al. |
| 6,508,815 B1 | 1/2003 | Strul et al. |
| 6,511,476 B2 | 1/2003 | Hareyama |
| 6,582,427 B1 | 6/2003 | Goble et al. |
| 6,620,157 B1 | 9/2003 | Dabney et al. |
| 6,632,193 B1 | 10/2003 | Davison et al. |
| 6,635,057 B2 | 10/2003 | Harano et al. |
| 6,648,883 B2 | 11/2003 | Francischelli et al. |
| 6,682,527 B2 | 1/2004 | Strul |
| 6,730,080 B2 | 5/2004 | Harano et al. |
| 6,733,498 B2 | 5/2004 | Paton et al. |
| 6,830,569 B2 | 12/2004 | Thompson et al. |
| 6,832,996 B2 | 12/2004 | Woloszko et al. |
| 6,855,141 B2 | 2/2005 | Lovewell |
| 6,855,142 B2 | 2/2005 | Harano et al. |
| 6,875,210 B2 | 4/2005 | Refior et al. |
| 6,939,347 B2 | 9/2005 | Thompson |
| 6,942,660 B2 | 9/2005 | Pantera et al. |
| 6,948,503 B2 | 9/2005 | Refior et al. |
| 6,989,010 B2 | 1/2006 | Francischelli et al. |
| 7,001,379 B2 | 2/2006 | Behl et al. |
| 7,001,381 B2 | 2/2006 | Harano et al. |
| 7,041,096 B2 | 5/2006 | Malis et al. |
| 7,074,217 B2 | 7/2006 | Strul et al. |
| RE39,358 E | 10/2006 | Goble |
| 7,172,591 B2 | 2/2007 | Harano et al. |
| 7,175,618 B2 | 2/2007 | Dabney et al. |
| 7,203,556 B2 | 4/2007 | Daners |
| 7,211,081 B2 | 5/2007 | Goble |
| 7,238,181 B2 | 7/2007 | Daners et al. |
| 7,244,255 B2 | 7/2007 | Daners et al. |
| 7,250,048 B2 | 7/2007 | Francischelli et al. |
| 7,258,688 B1 | 8/2007 | Shah et al. |
| 7,324,357 B2 | 1/2008 | Miura et al. |
| 7,367,972 B2 | 5/2008 | Francischelli et al. |
| D574,323 S | 8/2008 | Waaler |
| 7,407,502 B2 | 8/2008 | Strul et al. |
| 7,540,871 B2 | 6/2009 | Gonnering |
| 7,678,105 B2 | 3/2010 | McGreevy et al. |
| 7,717,909 B2 | 5/2010 | Strul et al. |
| 7,736,358 B2 | 6/2010 | Shores et al. |
| 7,799,020 B2 | 9/2010 | Shores et al. |
| RE41,921 E | 11/2010 | Goble |
| 7,846,156 B2 | 12/2010 | Malis et al. |
| 7,959,626 B2 | 6/2011 | Hong et al. |
| 7,972,329 B2 | 7/2011 | Refior et al. |
| 7,972,334 B2 | 7/2011 | McGreevy et al. |
| 7,972,335 B2 | 7/2011 | McGreevy et al. |
| 8,133,218 B2 | 3/2012 | Daw et al. |
| 8,551,082 B2 | 10/2013 | Strul et al. |
| 8,551,088 B2 | 10/2013 | Falkenstein et al. |
| 8,628,524 B2 | 1/2014 | Shilev |
| 8,751,013 B2 | 6/2014 | Johnson et al. |
| 8,764,741 B2 | 7/2014 | Dabney et al. |
| 8,915,910 B2 | 12/2014 | Falkenstein et al. |
| 8,951,248 B2 | 2/2015 | Messerly et al. |
| 8,956,349 B2 | 2/2015 | Aldridge et al. |
| 8,986,302 B2 | 3/2015 | Aldridge et al. |
| 8,998,891 B2 | 4/2015 | Garito et al. |
| 8,998,899 B2 | 4/2015 | Shilev et al. |
| 9,039,695 B2 | 5/2015 | Giordano et al. |
| 9,050,093 B2 | 6/2015 | Aldridge et al. |
| 9,060,765 B2 | 6/2015 | Rencher et al. |
| 9,060,775 B2 | 6/2015 | Wiener et al. |
| 9,060,776 B2 | 6/2015 | Yates et al. |
| 9,119,623 B2 | 9/2015 | Malis et al. |
| 9,144,453 B2 | 9/2015 | Rencher et al. |
| 9,168,054 B2 | 10/2015 | Turner et al. |
| 9,326,810 B2 | 5/2016 | Shilev et al. |
| 9,375,250 B2 | 6/2016 | Krapohl |
| 2002/0151884 A1 | 10/2002 | Hoey et al. |
| 2004/0097915 A1 | 5/2004 | Refior et al. |
| 2007/0203481 A1 | 8/2007 | Gregg et al. |
| 2007/0255271 A1 | 11/2007 | Dabney et al. |
| 2009/0069799 A1 | 3/2009 | Daw et al. |
| 2010/0063494 A1 | 3/2010 | Orszulak |
| 2012/0078139 A1 | 3/2012 | Aldridge et al. |
| 2013/0211398 A1 | 8/2013 | Daw et al. |
| 2014/0039482 A1 | 2/2014 | Strul et al. |
| 2015/0182276 A1 | 7/2015 | Wiener et al. |
| 2015/0182277 A1 | 7/2015 | Wiener et al. |
| 2015/0201990 A1 | 7/2015 | Shah et al. |
| 2015/0340586 A1 | 11/2015 | Wiener et al. |
| 2015/0366602 A1 | 12/2015 | Rencher et al. |
| 2016/0022347 A1 | 1/2016 | Rencher et al. |
| 2016/0089533 A1 | 3/2016 | Turner et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |

(56) References Cited

FOREIGN PATENT DOCUMENTS

| | | |
|---|---|---|
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0109602 A1 | 5/1984 |
| EP | 246350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 556705 A1 | 8/1993 |
| EP | 608609 A2 | 8/1994 |
| EP | 836868 A2 | 4/1998 |
| EP | 880220 A2 | 11/1998 |
| EP | 882955 A1 | 12/1998 |
| EP | 1036483 A2 | 9/2000 |
| EP | 1051948 A2 | 11/2000 |
| EP | 1366724 A1 | 12/2003 |
| EP | 1776929 A1 | 4/2007 |
| EP | 2103267 A1 | 9/2009 |
| EP | 2103269 A1 | 9/2009 |
| EP | 2283788 A1 | 2/2011 |
| EP | 2301462 A1 | 3/2011 |
| EP | 2474282 A2 | 7/2012 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| SU | 166452 | 1/1965 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006050888 A1 | 5/2006 |
| WO | 2008053532 A1 | 5/2008 |

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; 20.sup.th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.

(56) References Cited

OTHER PUBLICATIONS

U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/483,815, filed May 30, 2012, Jeffrey R. Unger.
U.S. Appl. No. 13/485,083, filed May 31, 2012, Robert J. Behnke, II.
U.S. Appl. No. 13/526,205, filed Jun. 18, 2012, Jeffrey L. Jensen.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Vald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Indium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
European Search Report dated Jul. 15, 2013 in European Application No. 13162304.
European Examination Report from Appl. No. 13162304.3 dated Nov. 26, 2015.

| PINS | 1 | 2 | 3 | 4 |
|---|---|---|---|---|
| a | RF_V_1 | RF_V_2 | RF_I_1 | RF_I_2 |
| b | TEMP_1 | TEMP_2 | SYS_V_1 | SYS_V_2 |
| c | SYS_I_1 | SYS_I_2 | PR_OK_1 | PR_OK_2 |
| d | STATUS_1 | STATUS_2 | CNTRL_1 | CNTRL_2 |

| PINS | 1 | 2 | 3 | 4 |
|---|---|---|---|---|
| a | RF_V_1 | TEMP_1 | RF_I_1 | SYS_V_1 |
| b | SYS_I_1 | PR_OK_1 | STATUS_1 | CNTRL_1 |
| c | RF_V_2 | TEMP_2 | RF_I_2 | SYS_V_2 |
| d | SYS_I_2 | PR_OK_2 | STATUS_2 | CNTRL_2 |

METHOD FOR EMPLOYING SINGLE FAULT SAFE REDUNDANT SIGNALS

CROSS-REFERENCE TO RELATED APPLICATIONS

This application is a divisional application of U.S. patent application Ser. No. 13/442,460, filed on Apr. 9, 2012, now U.S. Pat. No. 9,375,250, the entire contents of which are incorporated by reference herein.

BACKGROUND

1. Technical Field

The present disclosure is directed to electrosurgery. More particularly, the present disclosure is directed to an electrosurgical system and method for detecting single fault conditions in sensor assemblies.

2. Background of the Related Art

Devices containing electrical systems require various performance measures to ensure safety. Such safety requirements are particularly important in the case of medical equipment which comes into contact with a patient. Generally, one or more sensors collect data representing the operating condition of the system. After the sensors collect such data, a controller compares the collected data to predetermined threshold values in order to determine whether the system is operating in an unsafe condition.

Accordingly, there is a need for a system and method to mitigate the risk associated with single fault conditions in electrosurgical systems.

SUMMARY

As used herein, the phrases "in an embodiment," "in embodiments," "in some embodiments," or "in other embodiments," which may each refer to one or more of the same or different embodiments in accordance with the present disclosure. As used herein, a phrase in the form "A/B" means A or B. As used herein, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the term "RF" generally refers to electromagnetic waves having a lower frequency than microwaves. Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "ultrasound" generally refers to cyclic sound pressure with a frequency greater than the upper limit of human hearing.

As used herein, the term "sensor" generally refers to any sensing device capable of generating a signal representative of a value. As used herein, the term "processor" and "signal processing circuit" generally refers to an electronic circuit including analog and/or digital logic components capable of executing a set of instructions.

According to at least one aspect of the disclosure herein, an electrosurgical system includes a first sensor configured to output a first signal indicative of tissue property, a second sensor configured to output a second signal indicative of the tissue property, a signal processing circuit operatively coupled to the second sensor for receiving the second signal and outputting a processed signal, and a controller for receiving the first signal the first sensor and the processed signal from the signal processing circuit, wherein the controller compares the first signal to the processed signal.

According to yet another aspect of the disclosure herein, the signal processing circuit delays the second signal for a predetermined time period to generate the processed signal.

According to another aspect of the disclosure herein, the signal processing circuit inverts the second signal from an original waveform to the processed signal and outputs the processed signal.

According to yet another aspect of the disclosure herein, the controller turns off the system when the first signal and processed signal are identical.

According to another aspect of the disclosure herein, the controller converts the processed signal to the original waveform when the first signal and the processed signal are unique.

According to still another aspect of the disclosure herein, a method for employing single fault safe redundant signals for an electrosurgical system is disclosed and includes the step of providing a source of electrosurgical energy to treat tissue. The method further includes the steps of detecting an energy property using a first sensor and a second sensor; outputting a first voltage signal from the first sensor and a second voltage signal for the second sensor; processing the second voltage signal; and comparing the first voltage signal to the processed second voltage signal through the controller.

The method may further include the step of delaying the second voltage signal for a predetermined time period, on the step of inverting the second voltage signal from an original waveform to the processed second voltage signal.

The method may include the step of shutting down the system when the first voltage signal and processed second voltage signal are identical, or may further include the step of converting the second processed signal to the original waveform when the first voltage signal and processed second voltage signal are unique.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
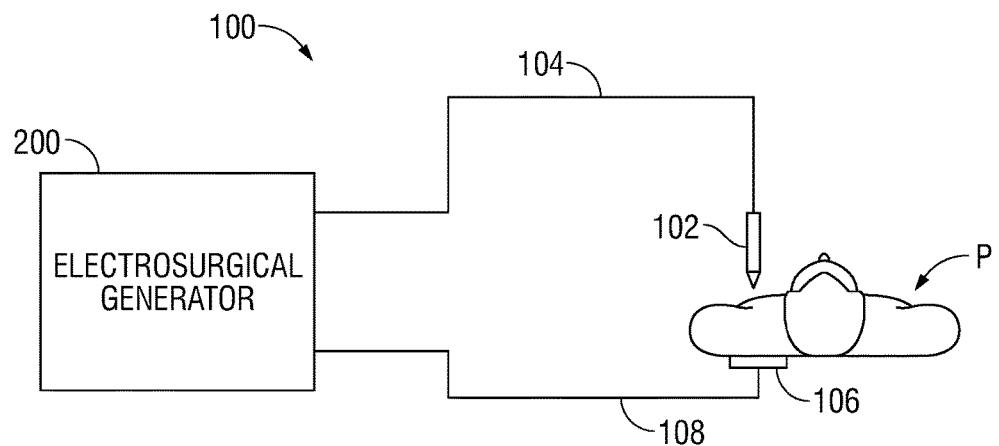
FIGS. 1A-1B are schematic block diagrams of electrosurgical systems in accordance with an embodiment of the present disclosure.

Particular embodiments of the present disclosure are described hereinbelow with reference to the accompanying drawings; however, it is to be understood that the disclosed embodiments are examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The generator according to the present disclosure can perform ablation, monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, ablation needle, ultrasonic transducers, etc.). Further, the generator includes electronic circuitry configured for generating microwave, radio frequency and/or acoustic energy specifically suited for various electrosurgical modes (e.g., cutting, blending, division, etc.) and procedures (e.g., ablation, monopolar, bipolar, vessel sealing).

FIG. 1A is a schematic illustration of a monopolar electrosurgical system 100 according to one embodiment of the present disclosure. The system 100 includes an electrosurgical instrument 102 having one or more electrodes for treating tissue of a patient P. The instrument 102 is a monopolar type instrument including one or more active electrodes (e.g., electrosurgical cutting probe, ablation electrode(s), etc.). Energy is supplied to the instrument 102 by a generator 200 via a supply line 104, which is connected to an active terminal (not explicitly shown) of the generator 200, allowing the instrument 102 to coagulate, ablate and/or otherwise treat tissue. The energy is returned to the generator 200 through a return electrode 106 via a return line 108 at a return terminal (not explicitly shown) of the generator 200. The active terminal and the return terminal are connectors configured to interface with plugs (not explicitly shown) of the instrument 102 and the return electrode 106, which are disposed at the ends of the supply line 104 and the return line 108, respectively.

The system 100 may include a plurality of return electrodes 106 that are arranged to minimize the chances of tissue damage by maximizing the overall contact area with the patient P. In addition, the generator 200 and the return electrode 106 may be configured for monitoring so-called "tissue-to-patient" contact to insure that sufficient contact exists therebetween to further minimize chances of tissue damage. In one embodiment, the active electrode 6 may be used to operate in a liquid environment, wherein the tissue is submerged in an electrolyte solution.

Figure 1B:
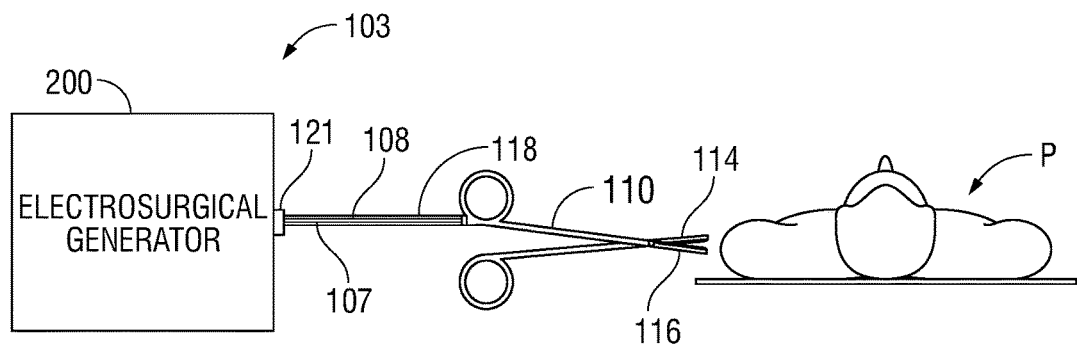

FIG. 1B is a schematic illustration of a bipolar electrosurgical system 103 according to the present disclosure. The system 103 includes a bipolar electrosurgical forceps 110 having one or more electrodes for treating tissue of a patient P. The electrosurgical forceps 110 include opposing jaw members having an active electrode 114 and a return electrode 116, respectively, disposed therein. The active electrode 114 and the return electrode 116 are connected to the generator 200 through cable 118, which includes the supply and return lines 104, 108 coupled to the active and return terminals. The electrosurgical forceps 110 are coupled to the generator 200 at a connector 121 having connections to the active and return terminals (e.g., pins) via a plug disposed at the end of the cable 118, wherein the plug includes contacts from the supply and return lines 104, 108. In other embodiments, generator 200 may be integrated into the forceps 110.

Figure 2:
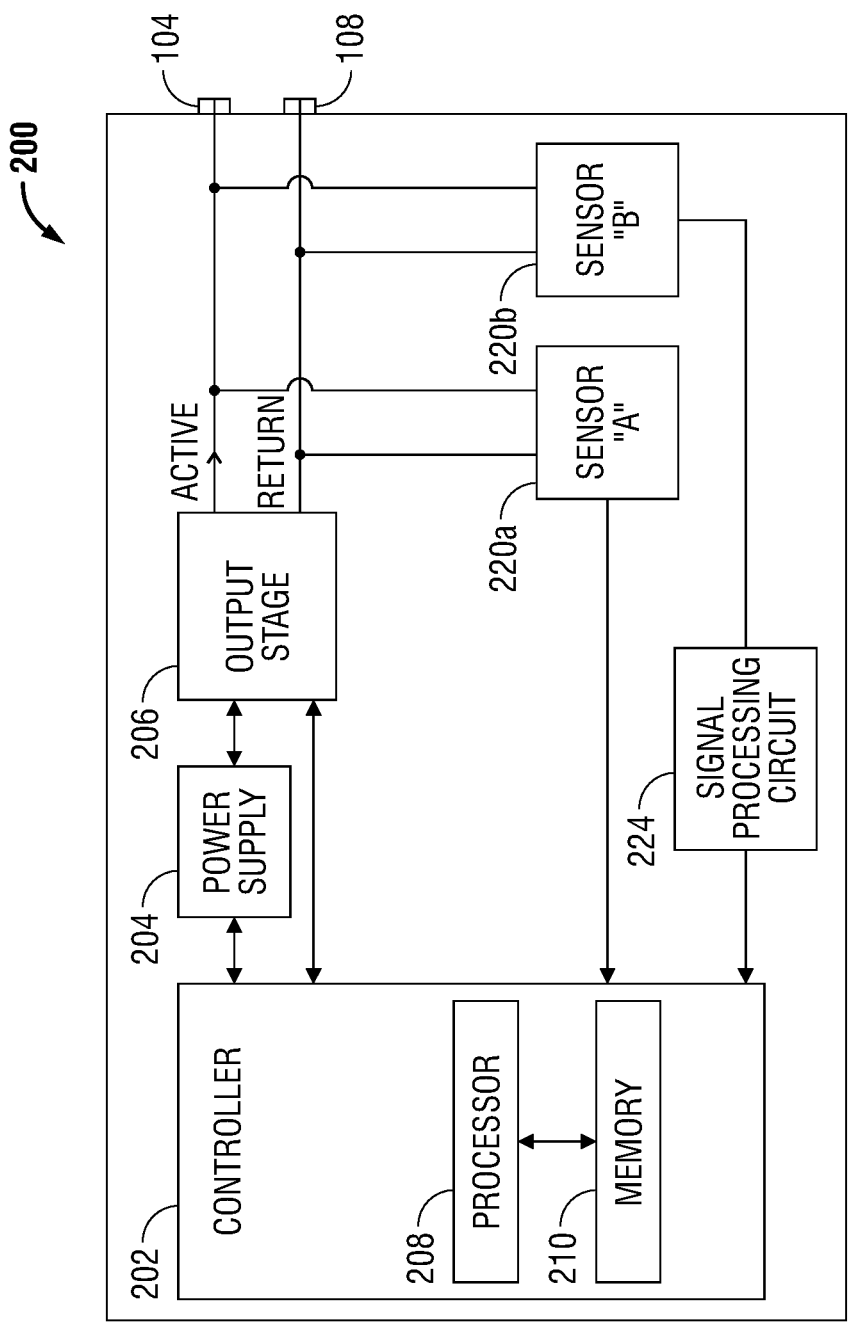
FIG. 2 is a block diagram view of an electrosurgical generator according to an embodiment of the present disclosure.

Referring to FIG. 2, the generator 200 includes a controller 202 for monitoring and controlling the generator 200, a power supply 204 ("HVPS"), which may be a high voltage DC power supply, and an output stage 206. The HVPS 204 is connected to an AC source (e.g., electrical wall outlet) and provides high voltage DC power to an output stage 206, which then converts high voltage DC power into treatment energy (e.g., laser, ultrasonic, electrosurgical or microwave) and delivers the energy to the active terminal 4. The energy is returned thereto via the return terminal 8. The output stage 206 is configured to operate in a plurality of modes, during which the generator 200 outputs corresponding waveforms having specific duty cycles, peak voltages, crest factors, etc. In another embodiment, the generator 200 may be based on other types of suitable power supply topologies.

Figures 3, 4A, 4B:
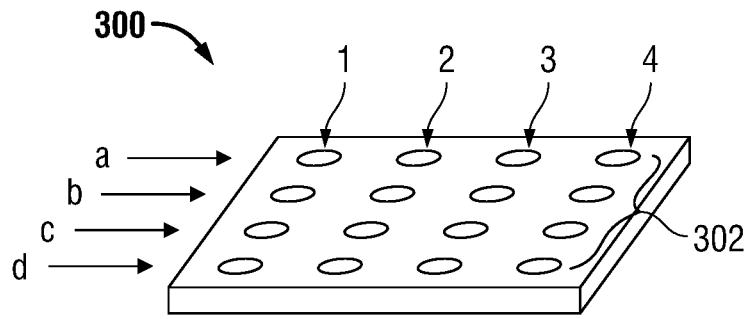
FIG. 3 is a perspective view of a processor according to the present disclosure.
FIGS. 4A and 4B are tables illustrating a grid array of the processor of FIG. 3 according to the present disclosure.

The controller 202 includes a processor 208 operably connected to a memory 210. The memory 210 may include non-transitory storage (e.g., flash media, disk media, etc.) and/or transitory (e.g., random-access memory) medium readable by a computer (e.g., controller 202) and includes, but is not limited to non-volatile type memory. The processor 208 includes one or more output ports that are connected to the HVPS 204 and/or output stage 206 allowing the processor 208 to control the output of the generator 200 according to either open and/or closed control loop schemes. Those skilled in the art will appreciate that the processor 208 may be substituted by any logic processor (e.g., control circuit) adapted to perform the calculations discussed herein. In embodiments, the processor 208 may be an integrated circuit as shown in FIG. 3, which is described in further detail below.

The generator 200 includes a plurality of sensors, namely, a first sensor 220a and a second sensor 220b that provide feedback to the controller 202. The sensors 220a and 220b measure tissue and/or energy property while the generator 200 is in use. Suitable tissue properties include temperature, real and/or imaginary impedance, conductivity, transmittance, opacity, and the like. Suitable energy properties include voltage, current, power, energy, phase, and the like. Non-limiting examples of sensors 220a and 220b suitable for measuring tissue and/or energy properties may include thermal sensors, electromagnetic field sensors, impedance monitors, optical sensors, transformers, capacitive sensors, and any combinations thereof.

In embodiments, the first sensor 220a and the second sensor 220b are configured to measure an identical tissue or energy property thereby providing redundant sensor signals to the controller 202. The sensors 220a and 220b output sensor signals indicative of the measured tissue or energy property as an analog electrical signal or a digital signal. The signal output by each of the sensors 220a and 220b are used to determine if generator 200 is functioning properly by comparing the two signals to detect a fault. The sensors 220a and 220b may be of substantially identical design and construction and produce substantially equivalent output signals.

The controller 202 determines a fault in the operation of the generator 200 by comparing redundant sensor signals from two or more sensors (e.g., sensors 220a and 200b) measuring an identical tissue and/or energy property. As part of a safety check, the controller 202 compares redundant output signals. If the controller 202 determines that the signals from the sensors 220a and 220b are substantially different, namely, the difference between the signals is greater than a predetermined threshold, then it is determined that a fault in the generator has occurred. However, this setup alone is unable to determine a single fault condition which may be caused by a physical short between the outputs of the sensors 220a and 220b and/or inputs from the sensors 220a and 220b at the controller 202, namely, the processor 208. In particular, the short results in the same signals being provided to the controller 202, which may lead to the controller 202 to incorrectly determine that the generator 200 is operating properly. In other words, regardless of a discrepancy in actual sensor readings, the controller 200 continues to receive substantially identical signals, namely, the difference between the signals is less than a predetermined threshold. As a result, the controller 202 determines incorrectly that there is no fault in the operation of the generator 200. This may result in an unsafe condition that is unacceptable for an electrosurgical system.

As described above, the first and second sensors 220a and 220b measures an identical tissue and/or energy property and output first and second signals, respectively. Electrosurgical generator 200 includes a signal processing circuit 224 operatively coupled to second sensor 220b. Signal processing circuit 224 is configured to modify the output received from second sensor 220b, thus converting the second signal to a processed signal. Signal processing circuit 224 may include any analog or digital components that can be used to convert the second sensor signal into the processed signal. Signal processing circuit 224 may modify the signal of the second sensor 220b by delaying, gain scaling, or phase inverting the signal before being received by controller 202. The signal processing circuit 224 may include any suitable circuit components such as operational amplifiers, integrators, and the like, to modify the signals.

Controller 202 receives the first signal from first sensor 220a and the processed signal from signal processing circuit 224. Controller 202 compares the two signals received to determine if a single fault condition exists. If the first signal and processed signal are different by a predetermined amount, the controller 202 establishes that no single fault exists and processed signal is converted into the original second signal. Thereafter, the controller 202 compares the first signal and the original second signal to determine if an output fault exists. If an output fault exists, then the controller 202 may either issue an alarm or terminate output of the generator 202. However, if the first signal and processed signal are identical, the controller 202 detects a single fault. In embodiments, the controller 202 may similarly issue an alarm and/or signal the generator 200 to shut down to prevent damage to the patient upon encountering single fault and/or output fault in the generator 200.

A single fault condition may occur as a result of a physical short developing within the hardware of generator 200. As described above, the controller 202 and/or the processor 208 may be an integrated circuit, or a chip 300 as shown in FIG. 3. The chip 300 includes a microelectronic device (e.g., processor 208) mounted on one side of a substrate. On the opposite side of the substrate is an array of contacts, which includes a plurality of connectors arranged in a two-dimensional grid array 302. Each contact provides the electrical connection between the chip 300 and a circuit board. In embodiments, the array 302 may be a ball grid array having a plurality of contact surfaces or a pin grid array having a plurality of pins configured to interface with corresponding connectors disposed on the circuit board. In further embodiments, the array 302 may be any other suitable surface-mount packaging used for integrated circuits.

The array 302 includes a plurality of columns, namely, columns 1, 2, 3, 4, and a plurality of rows, namely, rows, a, b, c, d. The present disclosure provides for a contact grid array configuration that minimizes incidence of single fault conditions. FIG. 4A shows a table of sensor signals provided to the chip 300. In this configuration, redundant sensor signals are being fed to adjacent pins, e.g., connectors a1 and a2, a3 and a4, b1 and b2, etc. In this configuration, adjacent pins receive signals from redundant components. However, there is a possibility that a short may be caused when these signals from redundant components are directed at adjacent pins.

As shown in FIG. 4B, the sensor signals provided to the chip 300 are rerouted such that redundant signals are positioned at non-adjacent pins. More specifically, the signal from the first sensor detecting voltage, RF_V_1, is positioned at pin a1. The redundant signal from second sensor, RF_V_2, is positioned at c1, thereby preventing a short occurring from two redundant signals at adjacent pins. Further, the first sensor detecting temperature at tissue site, TEMP_1, is positioned at a2 whereas the second sensor, TEMP_2, is positioned at c2. This configuration of controller 202 poses the greatest challenge for a short to occur as redundant pins are surrounded by pins receiving distinct signals on all sides. In this configuration, none of the redundant signals are provided to connectors disposed adjacent to each other. In other words, each of the connectors provided redundant signals corresponding to a first tissue and/or energy property is separated from its counterpart connector by one or more connectors receiving a signal corresponding to another tissue and/or energy property.

Further disclosed is a method for employing single fault redundant signals. The method has the step of detecting one or more redundant tissue properties using at least two sensors disposed on an electrosurgical instrument as described above. Each sensor provides a signal indicative of a tissue property or ambient property.

The method further includes the step of processing at least one sensor signal through a signal processing circuit by delaying for a predetermined time period, gain scaling, or phase inverting the signal to form a processed signal. Controller next compares the at least one sensor signal to the processed signal to determine if a single fault exists in the system.

The method may further include the step of shutting down the system when two signals are identical. The method may further include the step of converting the processed signal to the original sensor signal when the signals are unique. The method may further include comparing the original sensor signal to a redundant signal from a redundant sensor configured to measure the identical tissue and/or energy property and shutting down the system when the redundant sensor signals are substantially different.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figs. are presented only to demonstrate certain examples of the disclosure. Other elements, steps, methods, and techniques that are insubstantially different from those described above and/or in the appended claims are also intended to be within the scope of the disclosure.

What is claimed is:

1. An electrosurgical system for providing electrosurgical treatment energy, the system comprising:
    a first sensor configured to measure at least one property of electrosurgical energy and to output a first signal;
    a second sensor configured to measure the at least one property of the electrosurgical energy and to output a second signal;

a signal processing circuit operatively coupled to the second sensor, the signal processing circuit configured to receive the second signal, to modify the second signal, and to output a processed signal; and a controller configured to:
receive the first signal from the first sensor and the processed signal from the signal processing circuit;
compare the first signal and the processed signal;
convert the processed signal back to the second signal when a difference between the first signal and the processed signal exceeds a predetermined amount;
compare the first signal to the second signal converted from the processed signal; and
terminate an output of the electrosurgical system when the first signal and the processed signal are substantially identical.

2. The electrosurgical system according to claim 1, wherein the signal processing circuit is configured to delay the second signal for a predetermined period of time before outputting the processed signal.

3. The electrosurgical system according to claim 1, wherein the signal processing circuit is configured to invert the second signal to generate the processed second signal.

4. The electrosurgical system according to claim 1, wherein the controller is further configured to convert the processed signal back into the second signal when the first signal and the processed second signal are substantially different.

5. The electrosurgical system according to claim 1, wherein the controller is further configured to compare the first and second signals.

6. The electrosurgical system according to claim 1, wherein the controller is further configured to terminate output of the electrosurgical system in response to the first and second signals being substantially different.

7. The electrosurgical system according to claim 1, wherein the at least one property of the electrosurgical energy is at least one of voltage, current, power, energy, phase, or any combinations thereof.

8. The electrosurgical system according to claim 1, wherein at least one of the first sensor or the second sensor includes at least one of a thermal sensor, an electromagnetic field sensor, an impedance monitor, an optical sensor, a transformer, a capacitive sensor, or any combinations thereof.

9. An electrosurgical system for providing electrosurgical treatment energy, the system comprising:
a first sensor configured to measure at least one property of electrosurgical energy and to output a first signal;
a second sensor configured to measure the at least one property of the electrosurgical energy and to output a second signal;
a signal processing circuit operatively coupled to the second sensor, the signal processing circuit configured to receive the second signal, to modify the second signal, and to output a processed signal; and
a controller configured to:
receive the first signal from the first sensor and the processed signal from the signal processing circuit;
compare the first signal and the processed signal;
convert the processed signal back to the second signal when a difference between the first signal and the processed signal exceeds a predetermined amount;
compare the first signal to the second signal converted from the processed signal; and
terminate an output of the electrosurgical system in response to the first and second signals being substantially different.

10. The electrosurgical system according to claim 9, wherein the signal processing circuit is configured to delay the second signal for a predetermined period of time before outputting the processed signal.

11. The electrosurgical system according to claim 9, wherein the signal processing circuit is configured to invert the second signal to generate the processed second signal.

12. The electrosurgical system according to claim 9, wherein the controller is further configured to convert the processed signal back into the second signal when the first signal and the processed second signal are substantially different.

13. The electrosurgical system according to claim 9, wherein the controller is further configured to compare the first and second signals.

14. The electrosurgical system according to claim 9, wherein the at least one property of the electrosurgical energy is at least one of voltage, current, power, energy, phase, or any combinations thereof.

15. The electrosurgical system according to claim 9, wherein at least one of the first sensor or the second sensor includes at least one of a thermal sensor, an electromagnetic field sensor, an impedance monitor, an optical sensor, a transformer, a capacitive sensor, or any combinations thereof.

16. An electrosurgical system for providing electrosurgical treatment energy, the system comprising:
a first sensor configured to measure at least one property of electrosurgical energy and to output a first signal;
a second sensor configured to measure the at least one property of the electrosurgical energy and to output a second signal;
a signal processing circuit operatively coupled to the second sensor, the signal processing circuit configured to receive the second signal, to modify the second signal, and to output a processed signal; and
a controller configured to:
receive the first signal from the first sensor and the processed signal from the signal processing circuit;
compare the first signal and the processed signal;
convert the processed signal back to the second signal when a difference between the first signal and the processed signal exceeds a predetermined amount;
compare the first signal to the second signal converted from the processed signal; and
control an operation of the electrosurgical system based on at least one of the first signal, the second signal, or the processed signal.

17. The electrosurgical system according to claim 16, wherein the signal processing circuit is configured to delay the second signal for a predetermined period of time before outputting the processed signal.

18. The electrosurgical system according to claim 16, wherein the signal processing circuit is configured to invert the second signal to generate the processed second signal.

19. The electrosurgical system according to claim 16, wherein the controller is further configured to convert the processed signal back into the second signal when the first signal and the processed second signal are substantially different.

20. The electrosurgical system according to claim 16, wherein at least one of the first sensor or the second sensor includes at least one of a thermal sensor, an electromagnetic field sensor, an impedance monitor, an optical sensor, a transformer, a capacitive sensor, or any combinations thereof.

\* \* \* \* \*